(12) United States Patent
Bergt et al.

(10) Patent No.: US 10,195,083 B2
(45) Date of Patent: Feb. 5, 2019

(54) SECTIONING A TRANSPARENT MATERIAL USING OPTICAL RADIATION

(75) Inventors: Michael Bergt, Weimar (DE); Gregor Stobrawa, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 783 days.

(21) Appl. No.: 14/352,897

(22) PCT Filed: Aug. 7, 2012

(86) PCT No.: PCT/EP2012/065429
§ 371 (c)(1),
(2), (4) Date: Jun. 27, 2014

(87) PCT Pub. No.: WO2013/056867
PCT Pub. Date: Apr. 25, 2013

(65) Prior Publication Data
US 2014/0330260 A1    Nov. 6, 2014

(30) Foreign Application Priority Data

Oct. 21, 2011  (DE) .................. 10 2011 085 047

(51) Int. Cl.
| | |
|---|---|
| *A61B 18/20* | (2006.01) |
| *A61F 9/008* | (2006.01) |
| *B23K 26/38* | (2014.01) |
| *B23K 26/082* | (2014.01) |
| *B23K 103/00* | (2006.01) |

(52) U.S. Cl.
CPC ........ *A61F 9/00827* (2013.01); *B23K 26/082* (2015.10); *B23K 26/38* (2013.01); *A61F 2009/0087* (2013.01); *A61F 2009/00872* (2013.01); *A61F 2009/00878* (2013.01); *A61F 2009/00887* (2013.01);
(Continued)

(58) Field of Classification Search
CPC .............. A61F 9/00825; A61F 9/00827; A61F 2009/0087; A61F 2009/00887; A61F 2009/00889; A61F 2009/00897; B23K 26/08; B23K 26/082; B23K 26/362; B23K 26/382
USPC ............................. 606/4–6, 10–12; 128/898
See application file for complete search history.

(56) References Cited

U.S. PATENT DOCUMENTS

| | | |
|---|---|---|
| 4,901,718 A | 2/1990 | Bille et al. |
| 5,336,215 A | 8/1994 | Hsueh et al. |

(Continued)

FOREIGN PATENT DOCUMENTS

| | | |
|---|---|---|
| CN | 1154658 | 7/1997 |
| DE | 69500997 T2 | 4/1998 |

(Continued)

OTHER PUBLICATIONS

Lubatschowski, Holger et al., "Medical Applications for Ultrafast Laser Pulses", *RIKEN Review*, Japan, Jan. 2003, No. 50, p. 113-118.

*Primary Examiner* — Ahmed Farah
(74) *Attorney, Agent, or Firm* — Patterson Thuente Pedersen, P.A.

(57) ABSTRACT

A method for creating cuts in a transparent material using optical radiation, wherein the optical radiation is focused at a focus in the material and the focus is displaced along a trajectory, wherein a periodic, crossing Lissajous figure is used as trajectory as viewed perpendicular to a main direction of incidence at the radiation.

7 Claims, 8 Drawing Sheets

(52) U.S. Cl.
CPC . *A61F 2009/00897* (2013.01); *B23K 2103/32* (2018.08); *B23K 2103/50* (2018.08)

(56) References Cited

U.S. PATENT DOCUMENTS

| | | |
|---|---|---|
| 5,520,679 A | 5/1996 | Lin |
| 5,549,632 A | 8/1996 | Lai |
| 5,618,285 A | 4/1997 | Zair |
| 5,656,186 A | 8/1997 | Mourou et al. |
| 5,984,916 A | 11/1999 | Lai |
| 5,993,438 A | 11/1999 | Juhasz et al. |
| 6,110,166 A | 8/2000 | Juhasz |
| RE36,872 E * | 9/2000 | Zair ............... B23K 26/073 606/10 |
| 6,254,595 B1 | 7/2001 | Juhasz et al. |
| 6,325,792 B1 | 12/2001 | Swinger et al. |
| 6,497,701 B2 | 12/2002 | Shimmick et al. |
| 6,590,670 B1 | 7/2003 | Kato et al. |
| 6,607,527 B1 | 8/2003 | Ruiz et al. |
| 6,608,674 B2 | 8/2003 | Gerlach et al. |
| 7,101,364 B2 | 9/2006 | Bille |
| 7,486,409 B2 | 2/2009 | Yamashita et al. |
| 7,621,637 B2 | 11/2009 | Rathjen et al. |
| 8,740,889 B2 * | 6/2014 | Bissmann ........ A61F 9/00831 128/898 |
| 8,911,431 B2 * | 12/2014 | Reich ............... A61B 3/1173 606/4 |
| 2001/0031960 A1 | 10/2001 | Kliewer et al. |
| 2002/0035359 A1 | 3/2002 | Yee et al. |
| 2002/0173799 A1 | 11/2002 | Besharim et al. |
| 2003/0014042 A1 | 1/2003 | Juhasz et al. |
| 2003/0105457 A1 | 6/2003 | Mrochen et al. |
| 2004/0070761 A1 | 4/2004 | Horvath et al. |
| 2004/0199150 A1 | 10/2004 | Lai |
| 2004/0254568 A1 | 12/2004 | Rathjen |
| 2005/0107773 A1 * | 5/2005 | Bergt ............... B23K 26/08 606/4 |
| 2007/0179483 A1 | 8/2007 | Muhlhoff et al. |
| 2008/0077121 A1 | 3/2008 | Rathjen |
| 2009/0171329 A1 | 7/2009 | Raksi et al. |
| 2011/0022036 A1 | 1/2011 | Frey et al. |
| 2011/0034911 A1 | 2/2011 | Bischoff et al. |
| 2011/0071509 A1 | 3/2011 | Knox et al. |
| 2011/0224658 A1 * | 9/2011 | Bischoff ............ A61B 3/107 606/5 |
| 2011/0251601 A1 | 10/2011 | Bissmann et al. |
| 2011/0264081 A1 | 10/2011 | Reich et al. |
| 2012/0016352 A1 | 1/2012 | Dick et al. |
| 2012/0029492 A1 * | 2/2012 | Rathjen ............. A61F 9/00827 606/5 |
| 2013/0197634 A1 | 8/2013 | Palanker et al. |
| 2014/0330260 A1 * | 11/2014 | Bergt ............... B23K 26/38 606/5 |

FOREIGN PATENT DOCUMENTS

| | | |
|---|---|---|
| DE | 10034251 | 9/2001 |
| DE | 10124358 C1 | 10/2002 |
| DE | 10323422 | 4/2004 |
| DE | 10334108 A1 | 2/2005 |
| DE | 102008017293 A1 | 10/2009 |
| DE | 102008027358 A1 | 12/2009 |
| DE | 102008056488 A1 | 5/2010 |
| DE | 102008062658 A1 | 6/2010 |
| DE | 102009012873 A1 | 9/2010 |
| EP | 1159986 A2 | 5/2001 |
| EP | 1486185 | 12/2004 |
| JP | 2000-116694 | 4/2000 |
| JP | 06-277248 | 10/2006 |
| JP | 11-192253 | 9/2011 |
| WO | WO 93/16631 | 9/1993 |
| WO | WO 94/09849 A | 5/1994 |
| WO | WO 97/30752 | 8/1997 |
| WO | WO 98/14244 | 4/1998 |
| WO | WO 01/67978 A1 | 9/2001 |
| WO | WO 01/85075 A1 | 11/2001 |
| WO | WO 02/32353 A2 | 4/2002 |
| WO | WO 2003/059563 A2 | 7/2003 |
| WO | WO 2004/032810 A2 | 4/2004 |
| WO | WO 2006/074469 A2 | 7/2006 |
| WO | WO 2010/051975 A1 | 5/2010 |
| WO | WO 2010/070020 A2 | 6/2010 |
| WO | WO 2011/061160 A1 | 5/2011 |

\* cited by examiner

SECTIONING A TRANSPARENT MATERIAL USING OPTICAL RADIATION

RELATED APPLICATIONS

The present application is a National Phase entry of PCT Application No. PCT/EP2012/065429, filed Aug. 7, 2012, which claims priority from DE Application No. 102011085047.3, filed Oct. 21, 2011, said applications being hereby fully incorporated herein by reference in their entirety.

FIELD OF THE INVENTION

The invention relates to a method for sectioning a transparent material using optical radiation, wherein the optical radiation is focussed onto a focus in the material and the focus is shifted along a curved path.

The invention furthermore relates to a method for producing control data for a laser device which sections a transparent material by focussing optical radiation, wherein the control data predetermine a curved path for a shift of a focus of the optical radiation in the material.

Finally, the invention furthermore relates to a treatment apparatus for sectioning a transparent material, wherein the treatment apparatus has laser device, which is designed to create a cut in a transparent material by focussing optical radiation, and control device which is connected to the laser device and controls the laser device such that the laser device shifts a focus for the optical radiation in the material along a curved path.

BACKGROUND

Such methods and treatment apparatuses are known in the state of the art. In particular in the field of ophthalmology, such methods and treatment apparatus are used for procedures with which defective vision is corrected. The cuts can be used for example to modify the cornea such that defective vision is remedied. For example, methods are known in which a volume of the cornea is isolated and removed in order to modify the curvature and thus the imaging properties of the cornea to correct defective vision.

The creation of cuts on the eye is likewise necessary in cataract surgery. Within the framework of this surgery, a cloudy crystalline lens is removed. For this removal, it is advantageous to first section the lens in the lens bag, with the result that it can be removed through a small lateral access opening created surgically.

In these fields of use, as well as in other applications, optical radiation acts inside the material, for example the tissue, which is transparent to the optical radiation. Non-linear processes are usually used which require a focussing of treatment radiation, usually pulsed laser radiation, into the material, i.e. underneath the surface of the material. The creation of a cut then occurs by shifting the position of the focus in the material. It should be understood for the purposes of this description, that the shift of the focus does not necessarily require that radiation is also emitted into the focus at this time. In particular when pulsed laser radiation is used, the focus is continuously moved and laser radiation pulses are only emitted at certain times during the focus movement. Nevertheless the corresponding lens systems or pieces of device for focus movement generally move continuously, which is why the term "focus shift" here is also understood to mean the corresponding shift of the point at which optical radiation would be focussed even if such radiation is momentarily not emitted, e.g. between two laser pulses.

The accurate focussing of the laser radiation, i.e. a geometrically strongly delimited focus, is of great importance for non-linear effects, as only then can the necessary power densities in the material be achieved. This applies both to non-linear processes in which an individual focus already results in an interaction and to processes in which several laser radiation pulses which are emitted one after the other interact in order to achieve a material-cutting effect. In this regard, approaches are also known in which laser radiation pulses are emitted at several overlapping focus spots and only the interaction of the several laser radiation pulses in the overlap area leads to material cutting.

The necessary precise focussing of the laser radiation is understandably impaired by the material through which the laser radiation is guided. Since, as already mentioned, the focus lies inside the material when cuts are to be created in the material, cuts can obviously be generated with this principle as a rule only in a direction contrary to the main direction of incidence of the laser radiation, thus from posterior to anterior when used on the eye. Otherwise, parts of the material in which material has already been cut, thus the cut has been already partially constructed, would disrupt the passage of the laser radiation and thus the desired precise focussing. In other words, areas of the cut that are deeper in relation to the direction of incidence of the optical radiation must be cut before areas of the cut that are higher can be created.

A further problem which occurs with in the creation of cuts by guiding a focus along a path is the speed of the creation of cuts. The focus is usually deflected by means of scanning device. The deceleration, re-positioning or acceleration of the scanning device can substantially prolong the creation of cuts. When used on the eye, not only is this onerous for a patient, as the surgical procedure lasts longer, the expenditure that must be met for precautions against unintended eye movements also increases with the increasing time required for the creation of cuts.

This problem is particularly great when a sectioning of transparent material is to be carried out, thus crossing cuts are required. Because of the crossover points and the fact that the cuts must be constructed in layers contrary to the direction of incidence of the radiation, the deceleration, re-positioning and acceleration of the scanning device leads to a very great prolonging of the creation of cuts.

Although approaches are known in the state of the art for carrying out the deflection movements as continuously as possible, thus for dispensing with deceleration and acceleration processes for the deflection device as far as possible (cf. DE 102008027358 A1), these approaches are limited to quite particular cut geometries and in particular are not useful for sectioning material with crossing cuts.

SUMMARY OF THE INVENTION

An aspect of the invention is therefore to develop the method and the treatment apparatus of the type named at the outset such that a high sectioning speed can be achieved even when creating crossing cuts.

This is achieved according to the invention by a method for sectioning a transparent material using optical radiation, wherein the optical radiation is focussed onto a focus in the material and the focus is shifted along a path, wherein a periodic, crossing Lissajous figure is used as the path in a view perpendicular to a main direction of incidence of the radiation.

The object is likewise achieved according to the invention with a method for producing control data for laser device which sections a transparent material by focussing optical radiation, wherein the control data predetermine a path for a shift of a focus of the optical radiation in the material, wherein the control data are produced such that the path is a periodic, crossing Lissajous figure in a view perpendicular to a main direction of incidence of the radiation.

The object is likewise achieved according to the invention with a treatment apparatus for sectioning a transparent material, wherein the treatment apparatus has laser device, which is designed to create cuts in a transparent material by focussing optical radiation, and control device which is connected to the laser device and controls the laser device such that the laser device shifts a focus of the optical radiation in the material along a path, wherein the control device controls the laser device such that the path is a periodic, crossing Lissajous figure in a view perpendicular to a main direction of incidence of the radiation.

Thus a path is used which is a crossing and periodic Lissajous figure in a view perpendicular to the main direction of incidence of the radiation. The Lissajous figure has the advantage that a deflection device, which is usually realized as a biaxial scanner, moves according to harmonic oscillations. Usual scanning mirrors achieve their maximum operating speed precisely in this harmonic oscillation mode. The focus can thus be guided along the path at maximum speed if this path is a Lissajous figure. In order to create the desired, crossing cuts, a crossing Lissajous figure is used. In order to be able, in addition, to position the path in different depth positions in the material exactly one above the other, the Lissajous figure is periodic. Lissajous figures travelled in different depth positions then lie exactly one above the other and the desired cut is obtained.

A sectioning of material can, for one thing, be carried out by the focus position remaining constant in the direction along the direction of incidence of the optical radiation (so-called z-axis) for each pass through the Lissajous figure. The Lissajous figure is then moved one height level. Several passes are also conceivable, for example when working with pulsed laser radiation and when laser radiation pulses that follow each other in time are not to lie directly next to each other. Then, in one or further following passes, the holes that were left in the previous pass through the Lissajous figure can be filled with laser radiation pulses.

However, it is also possible to carry out the adjustment along the z-axis continuously, with the result that, although the periodic, i.e. closed, Lissajous figure appears when viewed along the main direction of incidence, in fact laser radiation pulses which were emitted in successive passes through the Lissajous figure are spaced apart a little in z-direction.

The crossing Lissajous figure particularly easily effects a sectioning of the material. The closed areas inside the Lissajous figure are then isolated material parts. If it is additionally desired still to cut these perpendicular to the main direction of incidence, it is expedient to design, according to a certain number of passes through the Lissajous figure, a cut, lying perpendicular to the main plane of incidence, which divides the parts created by the crossing Lissajous figure once again as seen in the depth direction.

The Lissajous figure is expediently created larger than the area in which the cuts are to be formed in the material. In the areas in which the Lissajous figure extends beyond this area, the optical radiation is preferably switched off or deactivated in respect of its material-cutting effect. This can be carried out for example by a deliberate defocussing, change of spectral parameters, attenuation of the pulse energy, extension of the pulse duration, etc. Rendering laser radiation pulses harmless is already known in the state of the art in another connection.

For this, it is favourable if an area of cut has been or is defined, the Lissajous figure is created or designed larger than the area of cut and the optical radiation on sections of the trajectory which lie outside of the area of cut is switched off or modified such that it does not create cuts in the transparent material. In the treatment apparatus, the control device controls the laser device analogously in areas in which the Lissajous figure lies outside of a predetermined area of cut such that the optical radiation is switched off or modified such that it does not create cuts in the transparent material.

Advantageously, the focus is additionally shifted along the main direction of incidence of the radiation and contrary to the main direction of incidence.

A crossing Lissajous figure is generated particularly easily by superimposing a first harmonic oscillation with a second harmonic oscillation, wherein both harmonic oscillations have frequencies which amount to integer multiples of a base frequency, and the frequency of the first oscillation is at least twice the base frequency. At least two integer multiples differ from each other. In the treatment apparatus, the control device then controls the laser device such that the crossing Lissajous figure is created by superimposing a first harmonic oscillation with a second harmonic oscillation, wherein both harmonic oscillations have frequencies which amount to integer multiples of a base frequency, and the frequency of the first oscillation is at least twice the base frequency.

The cuts can be formed particularly easily as a grid structure by providing the Lissajous figure repeatedly in several height levels lying one behind the other along a direction of incidence of the radiation. The control device of the treatment apparatus controls the laser device such that the cuts are formed as a grid structure by the Lissajous figure being provided repeatedly in several height levels lying one behind the other along a direction of incidence of the radiation.

The mentioned further separation of the areas cut by the Lissajous figure can be achieved by providing between at least two height levels an intermediate level, lying parallel to the height levels, in which a path is provided with which a cohesive cut is formed. The control device provides between at least two height levels an intermediate plane (for example lying parallel to the height planes) and controls the laser device such that a continuous cut is formed in the intermediate plane.

The treatment apparatus for example has a scanning device which has two scanning mirrors which deflect about axes that cross each other and focus-shifting device which moves the focus perpendicularly thereto and along the main direction of incidence, wherein the control device controls the focus-shifting device such that, after one pass through the Lissajous figure, the focus position is shifted contrary to the main direction of incidence by a distance to effect a contiguous material cutting of the successive passes through the Lissajous figure.

It is understood that the features mentioned above and those yet to be explained below can be used, not only in the stated combinations, but also in other combinations or singly, without departure from the scope of the present invention. The description of method features for material cutting or for producing control data likewise also relates to a corresponding embodiment of the control device which controls the treatment apparatus. Analogously, features which are described in respect of the treatment apparatus, in particular its control device, are likewise relevant for the corresponding method for treatment of material or producing control data.

The production of control data can be carried out separately from, i.e. independently of, the treatment and also of the treatment apparatus. Naturally, it presupposes corresponding knowledge about the treatment apparatus for which the control data are provided.

BRIEF DESCRIPTION OF THE DRAWINGS

The invention is explained in further detail below by way of example with reference to the attached drawings which also disclose features essential to the invention. There are shown in.

DETAILED DESCRIPTION

Figure 1:
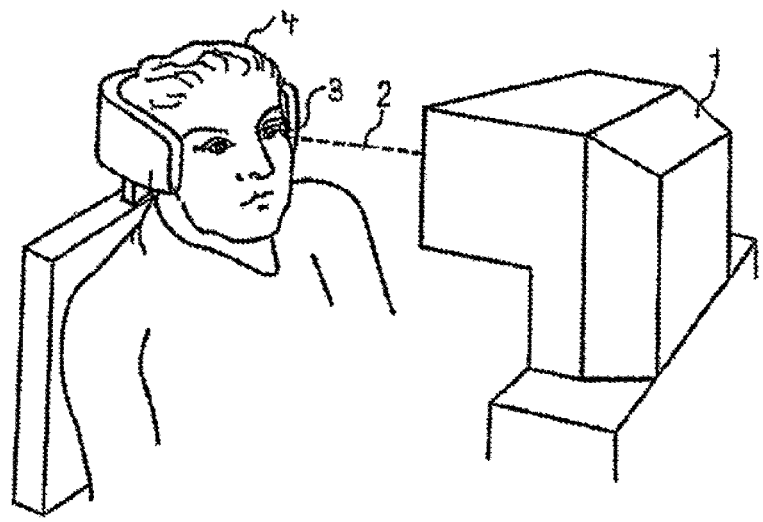
FIG. 1 is a schematic representation of a treatment apparatus for ophthalmology procedures, in particular for correcting defective vision.

FIG. 1 shows a treatment apparatus 1 for eye surgery. For example an eye-surgery process which is similar to that described in EP 1 159 986 A2 or U.S. Pat. No. 5,549,632 can be carried out with it. The treatment apparatus 1 creates a material cutting in transparent material using treatment laser radiation 2. This material cutting can be e.g. a creation of cuts, in particular the treatment apparatus for correcting defective vision can bring about a change on an eye 3 of a patient 4. The defective vision can include hyperopia, myopia, presbyopia, astigmatism, mixed astigmatism (astigmatism in which there is hyperopia in one direction and myopia in a direction at right angles thereto), aspheric errors and higher-order aberrations. The material cutting can, however, also be used in the field of ophthalmology on other tissues of the eye, e.g. for sectioning the crystalline lens in cataract surgery. Where reference is made to eye surgery below, this is to be understood in each case only by way of example and not as limiting.

In the embodiment example described, the components of the apparatus 1 are controlled by an integrated control unit, which, however, can of course also be formed as a stand-alone unit.

Figure 2:
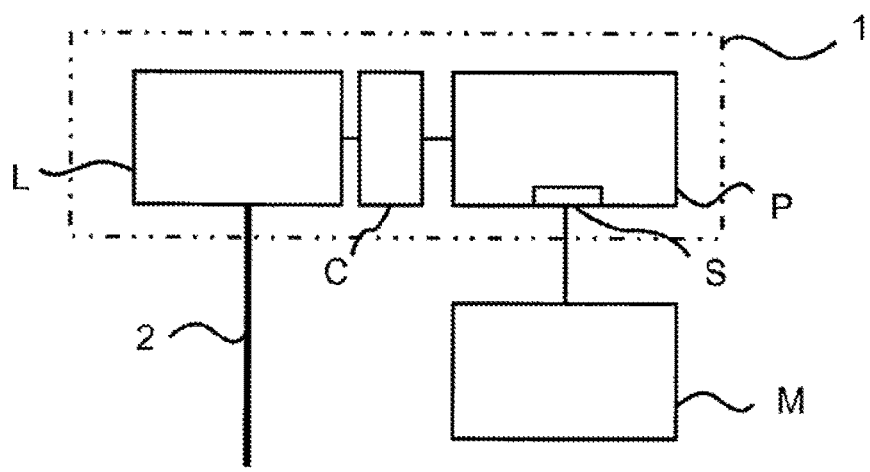
FIG. 2 is a schematic representation with regard to the structure of the treatment apparatus of FIG. 1.

FIG. 2 shows the treatment apparatus 1 schematically. In this variant it has at least three pieces of devices or modules. Laser device L emits the laser beam 2 onto the material, e.g. the eye 3, and adjusts the position of the focus in the material in three spatial directions x, y, z. The adjustment along the main direction of incidence of the optical radiation (z-axis) is called z-axis adjustment, the x- and y-axis adjustment is for example, carried out perpendicular to the z-axis by scanners.

The operation of the laser device L is fully automatic, controlled by integrated or separate control device C. In response to a corresponding start signal the laser device L starts to deflect the laser beam 2 and thereby creates cuts which are constructed in a manner yet to be described.

The control device C operates according to control data which either have been produced by it or have been supplied to it. In the latter case, which is shown in FIG. 2, the control data necessary for operation are supplied from a planning device P to the control device C beforehand as a control data set via control lines not identified in more detail. The determination or transmission of the control data takes place prior to operation of the laser device L. Naturally, the communication can also be wireless. As an alternative to direct communication, it is also possible to arrange the planning unit P physically separated from the laser device L, and to provide a corresponding data transmission channel.

In ophthalmology, the defective vision of the eye 3 is preferably measured with one or more pieces of measuring device M before the treatment apparatus 1 is used. The measured values are then supplied to the control device or the planning device P and form the basis for the production of the control data. In particular, the position and/or extent of an area to be treated, in particular to be sectioned, can be measured.

The control device or the planning device P produces the control data set from the measurement data which have been determined, e.g. for the eye to be treated. They are supplied to the planning device P via an interface S and, in the embodiment represented, come from measuring device M which has previously taken measurements of the eye of the patient 4. Naturally, the measuring device M can transfer the corresponding measurement data to the planning device P or directly to the control device C in any desired manner.

Preferably, the control data set is transmitted to the control device and, further preferably, operation of the laser device L is blocked until there [exits] exists a valid control data set at the laser device L. A valid control data set can be a control data set which in principle is suitable for use with the laser device L of the treatment apparatus 1. Additionally, however, the validity can also be linked to further tests being passed, for example whether details additionally stored in the control data set concerning the treatment apparatus 1, e.g. an apparatus serial number, or concerning the patient, e.g. a patient identification number, correspond to other details that for example have been read out or input separately at the treatment apparatus as soon as the patient is in the correct position for the operation of the laser device L.

The transmission of the measurement data and/or of the control data can be by means of memory chips (e.g. by USB or memory stick), magnetic storage (e.g. disks), or other data storage devices, by radio (e.g. WLAN, UMTS, Bluetooth) or wired connection (e.g. USB, Firewire, RS232, CAN-Bus, Ethernet etc.). A direct radio or wired connection has the advantage that the use of incorrect measurement data is ruled out with the greatest possible certainty. This applies in particular when the patient is transferred from the measuring device M or pieces of measuring device to the laser device L by means of a support device (not represented in the figure) which interacts with the measuring device M and the laser device L respectively such that the respective devices recognize whether the patient 4 is in the respective position for measurement or introduction of the laser radiation 2. The transmission of the measurement and defective-vision data to the treatment apparatus 1 can also take place simultaneously with bringing the patient 4 from the measuring device M to the laser device L.

According to one example embodiment, it is ensured by suitable means that the control device or the planning device P always produces the control data set belonging to the patient 4 and an erroneous use of an incorrect control data set for a patient 4 is as good as ruled out.

In the embodiment described, the laser radiation 2 is emitted as a pulsed laser beam focussed into the material, e.g. the eye 3. The pulse duration produced by the laser device L in this case is e.g. in the femto-second range, and the laser radiation 2 acts by means of non-linear optical effects in the material, e.g. the crystalline lens or cornea. The laser beam has e.g. 50 to 800 fs short laser pulses (for example 100-400 fs) with a pulse repetition frequency of between 10 kHz and 10 MHz. The type of material-cutting effect which the treatment apparatus 1 uses with the laser radiation, however, is of no further relevance for the following description, in particular there is no need to use pulsed laser radiation. The only important thing is that a focus of machining radiation 2 in the material is shifted along a path.

The treatment apparatus 1 forms a cut in the material, the shape of which cut depends on the pattern with which the laser-pulse foci are/become arranged in the tissue. The pattern in turn depends on the path along which the focus is shifted. The path predetermines target points for the focus position at which one or more laser pulse(s) is (are) emitted and ultimately defines the shape and position of the cut.

Figure 3:
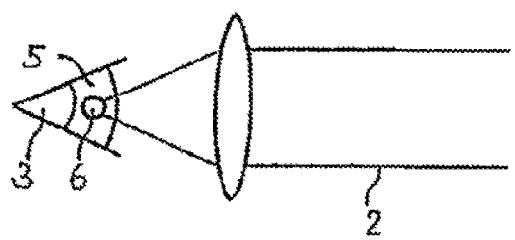
FIG. 3 depicts a basic principle for introducing pulsed laser radiation into the eye with the treatment apparatus of FIG. 1.

A possible mode of operation of the laser beam 2 is indicated schematically in FIG. 3. It is focussed into the material, e.g. the cornea 5 or lens of the eye, by means application of a lens system of the laser device L not identified in more detail. As a result there forms in the material a focus 6 in which the energy density of the laser radiation is so high that, in combination with the pulse length, a non-linear effect occurs. For example, each pulse of the pulsed laser radiation 2 can create at the respective site of the focus 6 an optical breakthrough in the material, e.g. in the cornea 5 or lens, which is indicated schematically in FIG. 3 by way of example by a plasma bubble. As a result, material, e.g. tissue, is cut owing to this laser pulse. When a plasma bubble forms, the tissue layer cutting comprises a larger zone than the spot covered by the focus 6 of the laser radiation 2, although the conditions for creating the breakthrough are achieved only in the focus. In order for an optical breakthrough to be created by every laser pulse, the energy density, i.e. the fluence, of the laser radiation must be above a certain threshold value which is dependent on pulse length. This relationship is known to a person skilled in the art from, for example, DE 695 00 997 T2.

Alternatively, a material-cutting effect can also be produced by the pulsed laser radiation by emitting several laser radiation pulses in one area, wherein the spots 6 overlap for several laser radiation pulses. Several laser radiation pulses then interact to achieve a tissue-cutting effect. For example the treatment apparatus 1 can use the principle which is described in WO 2004/032810 A2.

The treatment apparatus 1 creates in the cornea 5 or in the lens of the eye 1 a sectioning of the tissue by forming cuts as a grid (naturally, this is not limited to ophthalmology). By this grid represented schematically in FIG. 4, transparent material 1a is to be sectioned, with the result that it can be removed.

In the transparent material 1a, a grid of cuts 10, 11, 12 is created by shifting the focus 6 of the laser radiation 2, which propagates along a direction of propagation 3a, inside the transparent material 1a along a path 6a. The path 6a is chosen such that it follows the cuts 10, 11 and 12 and travels along these.

When controlling the laser device L, the control device C makes sure that the cuts 10, 11 and 12 are constructed by the trajectory 6a only contrary to the main direction of propagation 3a of the laser beam 2. Otherwise, the focus 6 would be disrupted by material cuts that are already present (for example cuts) in the incident light cone 4a. This problem is in principle posed in the case of material cutting by focussed optical radiation and is particularly great at crossover points 5a of the cuts 10, 11 and 12 in the use described by way of example.

The cut 12 represented by a dashed line illustrates that the path 6a has to be arranged in different height levels in order to avoid the mentioned laser focus disruption in the incident light cone 4a. The path 6a is therefore formed such that it works through all cuts 10, 11 and 12 in the lowest height level first, i.e. in the height level that is the furthest removed from the laser device L in relation to the main direction of incidence 3a. If, with the path 6a, the cut lines of all cuts 10, 11 and 12 were worked through with it in this height level, the same is carried out for the next height level which lies closer to the laser device L in relation to the main direction of incidence 3a.

Figure 4:
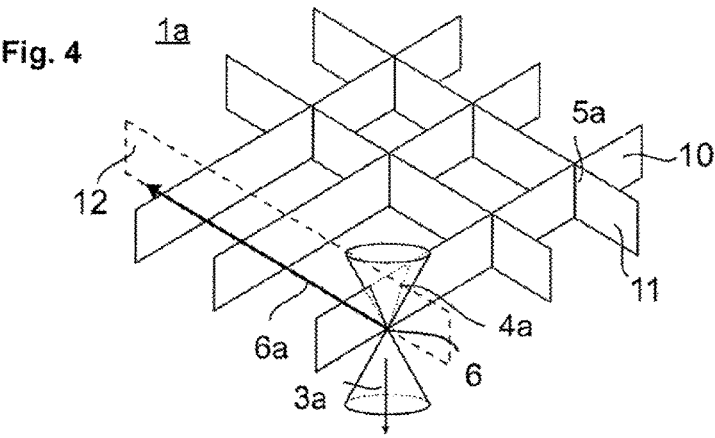
FIG. 4 is a schematic representation to illustrate a grid of cuts which is to be created with the treatment apparatus of FIG. 1.
Figure 5:
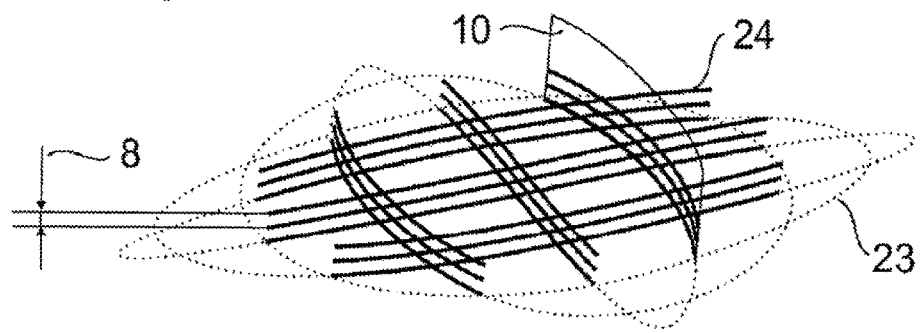
FIG. 5 is a schematic representation to illustrate the creation of the schematically represented cut of FIG. 4.

In order to avoid a time-consuming deceleration and re-positioning or acceleration of the focus deflection, the grid of cuts represented schematically in FIG. 4 is generated by movement of the biaxial deflection of the laser device L on a path 23 in the shape of a Lissajous figure, which is represented in FIG. 5. The Lissajous figure only has to be provided in respect of the x-/y-deflection, thus as seen along the main direction of incidence 3a. Only from this view does a closed, thus periodic, path 6a must occur.

There are thus two variants: Firstly, the path 6a can lie in one height plane. Then the z-position of the focus 6 remains constant as long as the Lissajous figure is travelled, and the path 6a is also closed in three-dimensional space. The control data or the control by the control device thus effect in each height level a closed path 23 on which the focus is guided. This is called variant 1 below.

Secondly, the z-adjustment can adjust the position of the focus, while the Lissajous figure is being travelled. This is called variant 2 below. Unless differences in these two variants are explicitly discussed, the statements made here apply to both variants.

As a Lissajous figure forms by a superimposition of harmonic oscillations, x-/y-deflection device with harmonic sine or cosine movements can be moved continuously. A high working speed is the result.

In sections 23 of the path 6a which run outside of the zone in which the intended cuts are to be created (the cut 10 is also drawn in by way of example in FIG. 5), the laser beam is blanked, i.e. switched off or deactivated in respect of its treatment effect. The laser radiation is active and cuts tissue only in sections 24 of the path 6a which run inside the zone in which cuts are to lie. FIG. 5 shows, dotted, the sections 23 of the path 6a, in which the laser beam is blanked. The sections 24 of the path 6a in which the radiation brings about a material cutting are drawn in with continuous lines.

FIG. 5 furthermore shows the spacing 8 between the height levels in which in each case the same Lissajous figure is travelled. The desired sectioning of the transparent material 1a achieved only when the path 6 follows Lissajous figures that are congruent in all individual height levels. In order to guarantee this feature, the Lissajous figure of the path 6a is a closed Lissajous figure in each height level.

The x-/y-deflection movement of the focus 6 follows the equations $$x = \sum_i A_x^i \cos(2\pi f_x^i t + \phi_x^i),$$

$$y = \sum_i A_y^i \cos(2\pi f_y^i t + \phi_y^i)$$

if the x- and y-scanners are controlled with control signals Sx and Sy according to the equations $$Sx = \sum_i a(f_x^i) A_x^i \cos(2\pi f_x^i t + \phi_x^i + \delta(f_x^i)),$$

$$Sy = \sum_i a(f_y^i) A_y^i \cos(2\pi f_y^i t + \phi_y^i + \delta(f_y^i))$$

For the sake of simplicity, a possible scaling factor which describes the proportionality between the amplitude of the deflection movement and the control signal is here assumed to be 1. The term i is to be understood as an index and not as a power.

In the equations a(f) describes a frequency-dependent amplitude attenuation and δ(f) describes a frequency-dependent phase retardation. Both of these frequency-dependent functions describe the response behaviour of the x-/y-deflection to the control signals. At very slow frequencies a=1 and δ=0 holds, and the scanners follow the control signals exactly. If the control frequencies rise, a(f) is reduced. The amplitude of the deflection movement thus becomes smaller than the controlling amplitude, and the phase retardation δ grows. The deflection movement follows the control signals only with some retardation. The frequency response from a and δ can be determined once for the scanner elements used and can be held available in the generation of the control signals.

In order to create the Lissajous figure in respect of the x-/y-deflection, integer multiples of a base frequency $f_0$ are chosen for all frequencies of the summands for x- and y-deflection, $$x = \sum_i A_x^i \cos(2\pi N_x^i f_0 t + \varphi_x^i),$$

$$y = \sum_i A_y^i \cos(2\pi N_y^i f_0 t + \varphi_y^i),$$

with $N_{xy}^i \in [1, 2, 3, \ldots]$, whereby the path 6a is repeated with the base frequency $f_0$.

To create the cuts 10, 11 and 12, according to variant 1 the path 6a can comprise, in each height level, one full pass (or, as mentioned in the general part of the description, several passes) through the Lissajous figure.

To create the cuts, according to variant 2 it is, however, likewise possible to carry out the shift along the main direction of incidence 3a during the Lissajous figure. The control device or the control data produced by the planning device effecting a z-adjustment of the focus 6 either in a short path section, which then represents a transition between two height levels of variant 1, or effecting a continuous z-adjustment of the focus 6. In relation to the above-mentioned equations, in which the scanning path is repeated with a base frequency $f_0$, the z-coordinate of the focus 6 moves, in the case of continuous z-adjustment of the focus 6, in the time period $1/f_0$, by the desired distance 8 which path sections lying one above the other are to have.

Figure 6:
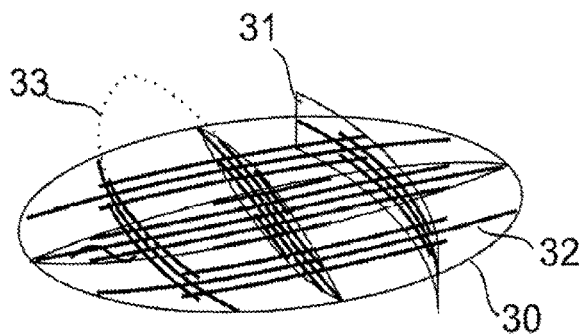
FIG. 6 is a representation similar to FIG. 5, but with a delimitation of cuts to a machining zone

FIG. 6 shows, by way of example, a sectioning of a crystalline lens 30, which is carried out for cataract surgery. The treatment apparatus 1 creates cuts 31, by the path 6a following a Lissajous figure. In sections 32 of the path which lie inside the lens 30, the laser radiation 2 is active. In sections 33 which lie outside of the crystalline lens 30, the laser radiation 2 is blanked. Naturally, this principle can also be applied to other materials and illustrates that the combination of activating the laser radiation inside a desired volume and blanking outside of the desired volume makes possible a rapid construction of crossing cuts.

The following features can additionally be realized:

The laser radiation can also be blanked on particular sections of the path inside an area in which cuts lie if the course of the path on the Lissajous figure in those areas does not correspond to a desired cutting pattern.

The height levels need not be planes in the mathematical sense. In particular in the case of a curvature of the image field and/or when curved material is machined, the height levels can be curved 2D manifolds.

In the control of scanners, the amplitude attenuation and phase retardation of the x-/y-deflection device can be determined and taken into account by providing corresponding counterbalancing offsets of the amplitude and phase of the deflection control at high frequencies.

The frequencies of the deflection on the Lissajous figures can take into account the maximum spacing of spots which successive laser pulses are to strike.

Naturally, the cutting pattern created with the Lissajous figure can be supplemented by further cut elements, for example a cylinder jacket as outer delimitation of the treated volume area. In order additionally to also divide the parts of the transparent material 1a created by the cuts 10, 11 and 12 perpendicular to the direction of propagation 3a, cuts which extend substantially perpendicular to the main direction of incidence 3a can also be created between individual height levels.

The cuts created using the Lissajous figure can be used to section eye tissue, for example the crystalline lens or the cornea. It is also possible to effect by the crossed cuts a targeted weakening of a material. In the field of eye surgery, this can be e.g. an intrastromal weakening of the cornea in order to influence the balance between intraocular pressure and cornea strength such that a desired change in the shape of the front surface of the cornea is achieved.

FIGS. 7 to 38 show examples of patterns which the Lissajous figure can have when viewed along the main axis of incidence 3a. Further patterns are also possible.

Figure 7:
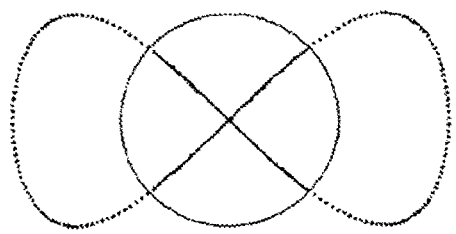
FIGS. 7-38 are schematic representations of paths which can be used in the creation of cuts according to FIG. 5 or 6 with the treatment apparatus of FIG. 1.
Figure 8:
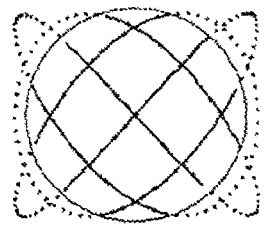
Figure 9:
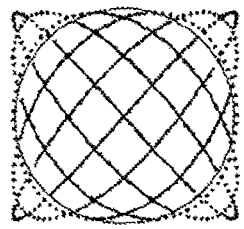
Figure 10:
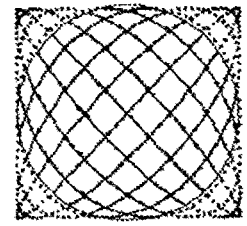
Figure 11:
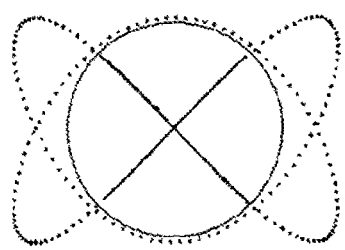
Figure 12:
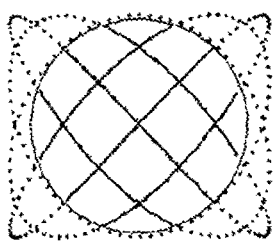
Figure 13:
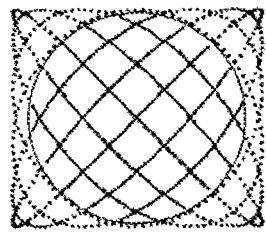
Figure 14:
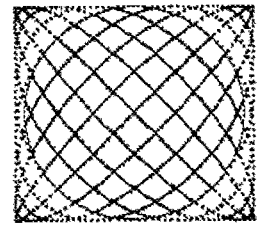
Figure 15:
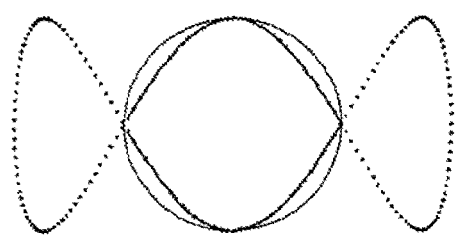
Figure 16:
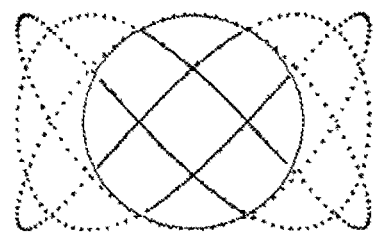
Figure 17:
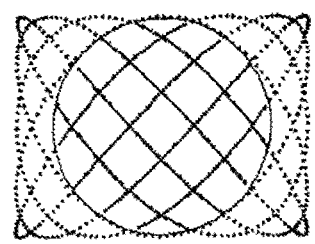
Figure 18:
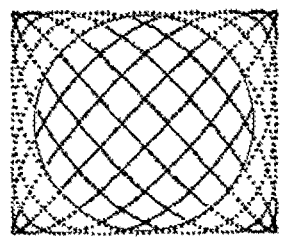

The Lissajous figures of FIGS. 7 to 18 are based on x-/y-deflection with single multiples of the base frequency, the Lissajous figures of FIGS. 19 to 38 are based on mixed multiples of the base frequency. The individual parameters are as follows:

|         | Nx | Ny | Ax   | Ay   | Φ       |
|---------|----|----|------|------|---------|
| FIG. 7  | 1  | 2  | 2    | 1    | 90°     |
| FIG. 8  | 3  | 4  | 1.1  | 0.95 | 30°     |
| FIG. 9  | 5  | 6  | 1.02 | 0.96 | 18°     |
| FIG. 10 | 7  | 8  | 1.01 | 0.97 | 12.86°  |
| FIG. 11 | 2  | 3  | 1.5  | 1.05 | 45°     |
| FIG. 12 | 4  | 5  | 1.25 | 1    | 22.5°   |
| FIG. 13 | 6  | 7  | 1.15 | 1.03 | 15°     |
| FIG. 14 | 8  | 9  | 1.09 | 1.01 | 11.25°  |
| FIG. 15 | 1  | 3  | 2    | 1    | 90°     |
| FIG. 16 | 3  | 5  | 1.6  | 1.01 | 30°     |
| FIG. 17 | 5  | 7  | 1.33 | 1.02 | 18°     |
| FIG. 18 | 7  | 9  | 1.2  | 1.03 | 12.86°  |

Figure 19:
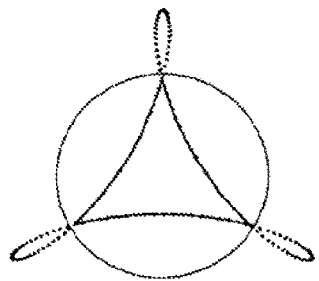
Figure 20:
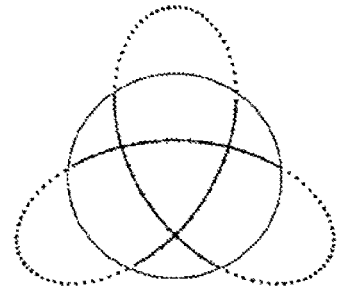
Figure 21:
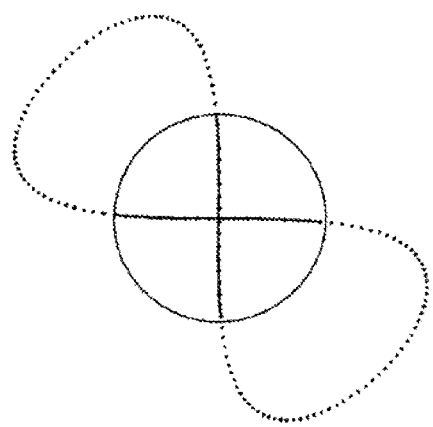
Figure 22:
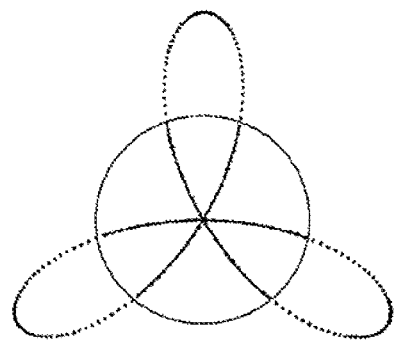
Figure 23:
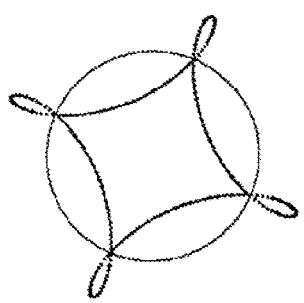
Figure 24:
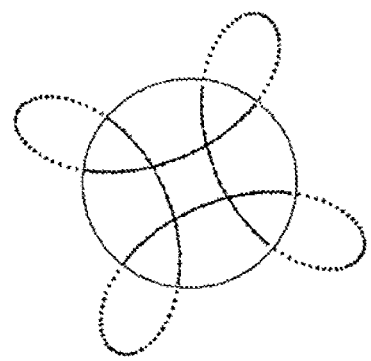
Figure 25:
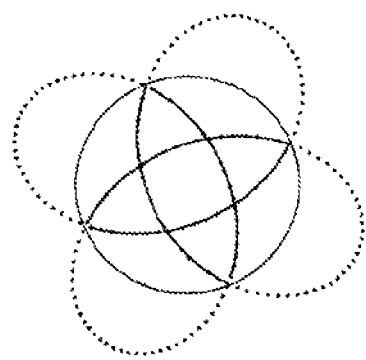
Figure 26:
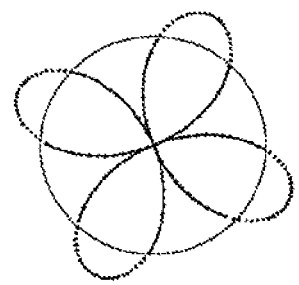
Figure 27:
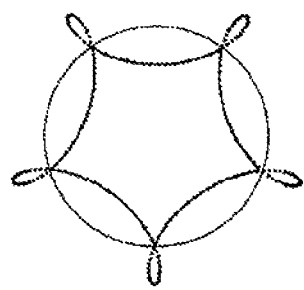
Figure 28:
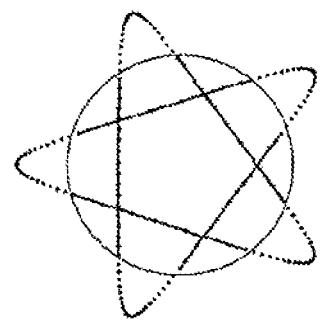
Figure 29:
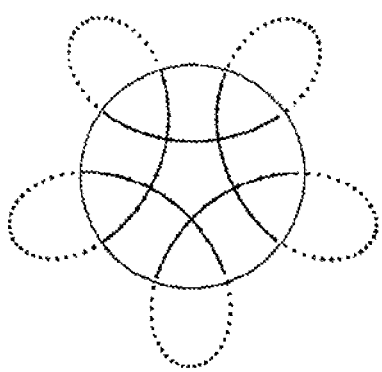
Figure 30:
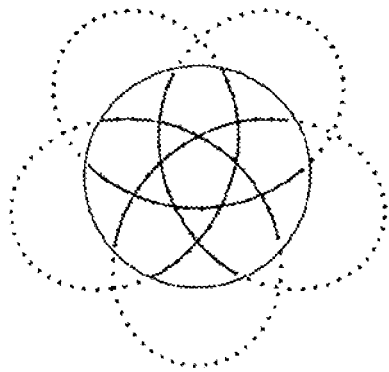
Figure 31:
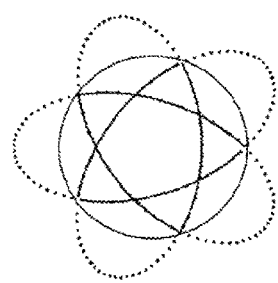
Figure 32:
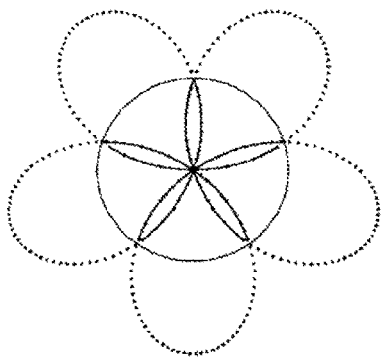
Figure 33:
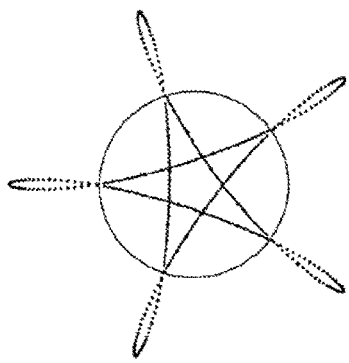
Figure 34:
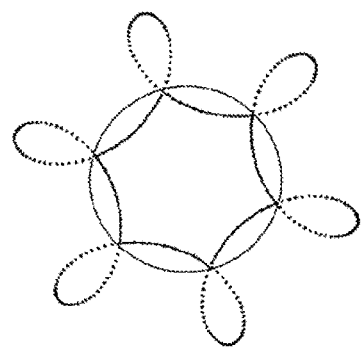
Figure 35:
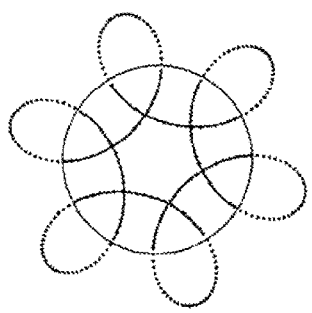
Figure 36:
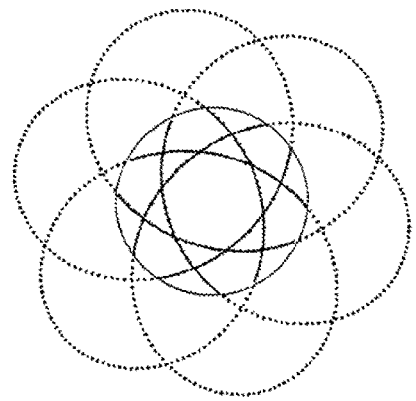
Figure 37:
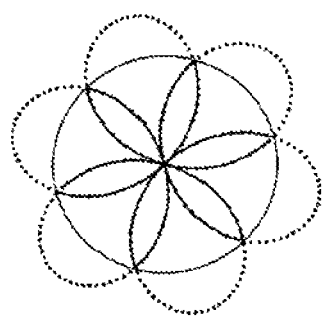
Figure 38:
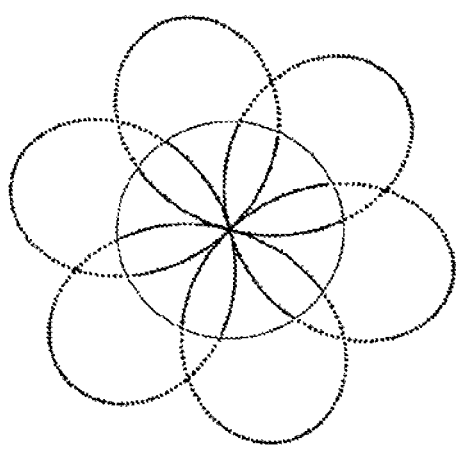

|         | $N_x^i$ | $N_y^i$ | $A_x^i$    | $A_y^i$    | $\Phi_x^i$ | $\Phi_y^i$ |
|---------|---------|---------|------------|------------|------------|------------|
| FIG. 19 | 1; 2    | 1; 2    | 1; 0.63    | 1; 0.63    | 0°; 90°    | 90°; 0°    |
| FIG. 20 | 1; 2    | 1; 2    | 0.65; 1    | 0.65; 1    | 0°; 90°    | 90°; 0°    |
| FIG. 21 | 1; 2    | 1; 2    | 1.5; 0.75  | 1.5; 0.75  | 0°; 270°   | 0°; 90°    |
| FIG. 22 | 1; 2    | 1; 2    | 1; 1       | 1; 1       | 0°; 90°    | 90°; 0°    |
| FIG. 23 | 1; 3    | 1; 3    | 1; 0.45    | 1; 0.45    | 0°; 90°    | 90°; 0°    |
| FIG. 24 | 1; 3    | 1; 3    | 1; 0.75    | 1; 0.75    | 0°; 90°    | 90°; 0°    |
| FIG. 25 | 1; 3    | 1; 3    | 0.64; 1    | 0.64; 1    | 0°; 90°    | 90°; 0°    |
| FIG. 26 | 1; 3    | 1; 3    | 0.65; 0.65 | 0.65; 0.65 | 0°; 90°    | 90°; 0°    |
| FIG. 27 | 1; 4    | 1; 4    | 1; 0.35    | 1; 0.35    | 0°; 90°    | 90°; 0°    |
| FIG. 28 | 2; 3    | 2; 3    | 1; 0.45    | 1; 0.45    | 0°; 90°    | 90°; 0°    |
| FIG. 29 | 1; 4    | 1; 4    | 1; 0.7     | 1; 0.7     | 0°; 90°    | 90°; 0°    |
| FIG. 30 | 1; 4    | 1; 4    | 0.7; 1     | 0.7; 1     | 0°; 90°    | 90°; 0°    |
| FIG. 31 | 2; 3    | 2; 3    | 0.5; 1     | 0.5; 1     | 0°; 90°    | 90°; 0°    |
| FIG. 32 | 1; 4    | 1; 4    | 1; 1       | 1; 1       | 0°; 90°    | 90°; 0°    |
| FIG. 33 | 2; 3    | 2; 3    | 1.1; 0.85  | 1.1; 0.85  | 0°; 90°    | 90°; 0°    |
| FIG. 34 | 1; 5    | 1; 5    | 1.3; 0.55  | 1.3; 0.55  | 0°; 90°    | 90°; 0°    |
| FIG. 35 | 1; 5    | 1; 5    | 1; 0.6     | 1; 0.6     | 0°; 90°    | 90°; 0°    |
| FIG. 36 | 1; 5    | 1; 5    | 0.8; 1.3   | 0.8; 1.3   | 0°; 90°    | 90°; 0°    |
| FIG. 37 | 1; 5    | 1; 5    | 0.7; 0.7   | 0.7; 0.7   | 0°; 90°    | 90°; 0°    |
| FIG. 38 | 1; 5    | 1; 5    | 1; 1       | 1; 1       | 0°; 90°    | 90°; 0°    |

The following example is given for determining the path:

The path 6a shall section a circular zone with a diameter of e.g. 5 mm over a height extension of e.g. 1 mm according to FIG. 12 into e.g. 4×4 sections. A maximum distance of e.g. ds=3 μm of neighbouring laser pulse positions and dT=3 μm of two paths lying one above the other in the main direction of incidence is to be observed. The laser device L emits laser pulses e.g. with a frequency $f_L$=500 kHz. The speed v of the movement of the scanner position should not exceed v=ds*f=1.5 m/s, but should, as far as possible, lie at this maximum to achieve a short treatment time.

The following applies to the speed along the path:

$$v = \sqrt{\dot{x}^2 + \dot{y}^2},$$

wherein $\dot{x}$, $\dot{y}$ are the time derivatives of the x- and y-coordinates of the focus position.

With $$x = A_x \cos(2\pi f_0 N_x t), y = A_y \cos(2\pi f_0 N_y t + \varphi) \text{ (by way of example } x=0\text{)}$$

the time derivatives are:

$$\dot{x} = -2\pi f_0 N_x A_x \sin(2\pi f_0 N_x t), \dot{y} = -2\pi f_0 N_y A_y \sin(2\pi f_0 N_y t + \varphi).$$

The speed v becomes maximum at time t, if the sine term of both $\dot{x}$ and $\dot{y}$ assume the maximum value 1 or −1 and is then:

$$\hat{v} = 2\pi f_0 \sqrt{(N_x A_x)^2 + (N_y A_y)^2}.$$

The cosine terms of x and y are then precisely 0 and the laser focus is then located exactly on an optical axis defining the main direction of incidence. At the position v does not quite achieve the maximum value $\hat{v}$ but is upwardly limited by it and can be estimated without great errors by $\hat{v}$ (e.g. for the path according to FIG. 16).

The dimensions of the path is set via the amplitudes $A_x$ and $A_y$. The minimum dimension is to cover the 5-mm diameter area. To create cuts which cross perpendicularly on the optical axis <x,y>=<0,0>, there must be at the axis position $\dot{x}=\pm\dot{y}$, thus $N_x A_x = N_y A_y$.

To generate the depicted FIG. 12, an $N_x$ of 4 and an $N_y$ of 5 are necessary. $A_y$ must correspond to the desired diameter of e.g. 5 mm, and $A_x$ then is $A_x = N_y A_y / N_x = 6.25$ mm. With these values, 222.14 mm*$f_0$ is calculated for $\hat{v}$.

Thus if v=1.5 m/s is to be achieved, the periodic path must be repeated with $f_0$=6.75 Hz. For the scanners, the cosine frequencies follow $f_x$=4*6.75 Hz=27 Hz and $f_y$=33.75 Hz, which is set e.g. in the case of mirrors driven by galvanometer. For a height of 1 mm and with a distance between paths lying one above the other of dT=3 μm, 333 passes through the path are stacked above the other. At $f_0$=6.75 Hz, this takes barely 50 s.

The base frequency is found analogously for the remaining Lissajous figures or other geometric constraints, assuming the given or desired boundary conditions. E.g. for FIG. 8 with otherwise identical parameters results in a base frequency $f_0$=9.5 Hz introducing the 333 cutting levels could be introduced in 35 s.

The size of the parts which are created in the material by the sectioning depends, as FIGS. 7 to 38 show, on the Lissajous figure used. If the side length of a part is denoted q and the radius of the zone in which the sectioning is to take place (circle in FIGS. 7 to 38) is denoted r, the following applies to FIGS. 7-10: q=2*r/$N_y$
FIGS. 11-14: q=2*r/$N_x$
FIGS. 15-18: q=2*r/$N_x$

The invention claimed is:

1. A method for sectioning a crystalline lens or a lens capsule of the eye using optical radiation, comprising:
   focusing the optical radiation along a main direction of incidence and at a focus located within the material; and
   chopping a volume of the crystalline lens or the lens capsule of the eye by cuts having a grid structure by shifting the focus along a path having the form of a crossing Lissajous figure perpendicular to the main direction of incidence and by repeating the Lissajous figure either at several height levels that are stacked along the direction of incidence or while adjusting the focus along the direction of incidence.

2. The method according to claim 1, further comprising additionally shifting the focus back-and-forth along the main direction of incidence of the radiation.

3. The method according to claim 1, further comprising creating the Lissajous figure by superimposing a first harmonic oscillation with a second harmonic oscillation, wherein both harmonic oscillations have frequencies which amount to different integer multiples of a base frequency, and the frequency of the first oscillation is at least twice the base frequency.

4. The method according to claim 3, wherein the frequency of the first oscillation is at least three times the base frequency.

5. The method according to claim 1, further comprising using the Lissajous figure to defines a cut area such that the Lissajous figure comprises sections of the path extending beyond said cut area and the optical radiation is switched off or modified on said sections of the path extending beyond said cut area such that it does not create cuts in the transparent material on said sections of the path extending beyond said cut area.

6. The method according to claim 1, wherein the cuts have a grid structure and further comprising repeating the Lissajous figure in several height levels that are stacked along the direction of incidence.

7. The method according to claim 6, further comprising providing, between at least two height levels, an intermediate plane lying parallel to the height levels and forming a contiguous cut surface in the intermediate plane.

* * * * *

UNITED STATES PATENT AND TRADEMARK OFFICE
CERTIFICATE OF CORRECTION

| | | |
|---|---|---|
| PATENT NO. | : 10,195,083 B2 | Page 1 of 1 |
| APPLICATION NO. | : 14/352897 | |
| DATED | : February 5, 2019 | |
| INVENTOR(S) | : Michael Bergt et al. | |

It is certified that error appears in the above-identified patent and that said Letters Patent is hereby corrected as shown below:

Column 12, Line 64, In Claim 5 delete "defines" and insert --define--

Signed and Sealed this
Eleventh Day of June, 2019

Andrei Iancu
*Director of the United States Patent and Trademark Office*

UNITED STATES PATENT AND TRADEMARK OFFICE
CERTIFICATE OF CORRECTION

PATENT NO. : 10,195,083 B2
APPLICATION NO. : 14/352897
DATED : February 5, 2019
INVENTOR(S) : Michael Bergt et al.

It is certified that error appears in the above-identified patent and that said Letters Patent is hereby corrected as shown below:

On the Title Page

In the Abstract:
In the last line, delete "at" and insert --of--

In the Specification

Column 6, Line 42, delete "[exits]"

Column 6, Lines 63/64, there should not be a new paragraph

Signed and Sealed this
Twentieth Day of August, 2019

Andrei Iancu
*Director of the United States Patent and Trademark Office*